United States Patent [19]

Grosse et al.

[11] 4,427,603
[45] Jan. 24, 1984

[54] PROCESS FOR MAKING PHOSPHONIC ACID ESTER CHLORIDES

[75] Inventors: Jürgen Grosse, Hürth; Werner Pieper, Erftstadt, both of Fed. Rep. of Germany

[73] Assignee: Hoechst Aktiengesellschaft, Fed. Rep. of Germany

[21] Appl. No.: 379,304

[22] Filed: May 18, 1982

[30] Foreign Application Priority Data

May 20, 1981 [DE] Fed. Rep. of Germany ....... 3120069

[51] Int. Cl.$^3$ ............................................. C07F 9/14
[52] U.S. Cl. .................................. 260/969; 260/960
[58] Field of Search .............................. 260/969, 960

[56] References Cited

PUBLICATIONS

Houben–Weyl, "Methoden der Organ ischen Chemie", vol. XII, No. 1, (1963), pp. 415–420.

Primary Examiner—Anton H. Sutto
Attorney, Agent, or Firm—Connolly and Hutz

[57] ABSTRACT

The disclosure relates to a process for making phosphonic acid ester chlorides of the general formula (I)

R—P(O) ClOR'           (I)

in which R stands for an alkyl group with 1 to 6 carbon atoms or an aryl group and R' stands for an alkyl group with 1 to 20 carbon atoms or an aryl group. More particularly, a compound of general formula (II)

R—PCl$_2$           (II)

is reacted with a sulfuric acid monoester of general formula (III)

R'—O—SO$_3$H           (III)

R and R' in formulae (II) and (III) having the meanings given above; the reactants are used in about equimolar proportions and the reaction is effected at a temperature of from −20° C. to 50° C. After termination of the reaction, the phosphonic acid ester chloride is separated from the reaction mixture by subjecting this latter to distillation under vacuum.

7 Claims, No Drawings

PROCESS FOR MAKING PHOSPHONIC ACID ESTER CHLORIDES

The present invention relates to a process for making phosphonic acid ester chlorides by subjecting alkyl or aryldichlorophosphanes to oxidation.

The manufacture of phosphonic acid ester chlorides by a variety of processes, referred to as processes 1 to 6 hereinafter, has been broadly described in "Methoden der organischen Chemie" (Houben-Weyl), volume XII/1, 4th edition (1963), pages 415–420.

Process 1 provides for a phosphonic acid dialkylester to be reacted with PCl$_5$ in accordance with the following reaction equation:

R—P(O)(OR')$_2$+PCl$_5$→R—P(O)(OR')Cl-
+POCl$_3$+RCl

This reaction entails the formation of by-products, namely phosphonic acid dichlorides which are partially obtained in considerable quantities and are very difficult to separate distillatively. In carrying out this reaction, it is possible for the PCl$_5$ to be replaced by thionyl chloride which, however, is less suitable than PCl$_5$.

In process 2, phophonic acid dihalides are subjected to reaction with equimolar proportions of an alcohol or phenol in the presence of a tertiary amine, such as pyridine or trimethylamine, to undergo conversion to phosphonic acid ester halides. During the reaction, ammonium salts of the amines are obtained as useless by-products which naturally affect the economy of the process.

Process 3 relates to a reaction which is illustrated by the following equation:

[R—PCl$_3$⊕]AlCl$_4$⊖+2R'OH→R—P(O)-
(OR')Cl+R'Cl+R'Cl+2HCl+AlCl$_3$

This process cannot reasonably be carried out under commercial conditions, last but not least in view of the fact that desirable final product is obtained in yields as low as about 32%, depending on the nature of the particular alcohol used.

In special cases, it is possible to react phosphonic acid monohalides which exist for a short while only with a sulfuric acid dialkylester to obtain phosphonic acid alkylester halides. Needless to say, this process 4 has equally failed to gain commercial interest.

Processes 5 and 6 also lack commercial interest, for economical reasons. Process 5 provides for phosphonous acid monoesters to be converted by treatment with chlorine or sulfuryl chloride to phosphonic acid ester chlorides which are obtained in a yield of 36%. Process 6 finally provides for aliphatic hydrocarbons to be subjected to oxidative chlorophosphonation with the resultant formation of phosphonic acid ester chlorides which however are obtained in low yields only. In addition to this, equimolar proportions of phosphoric acid ester dichlorides are obtained as by-products in this reaction.

The present invention now provides a process which permits the adverse effects entailed by the methods described heretofore to be avoided.

The present invention relates more particularly to a process for making phosphonic acid ester chlorides of the general formula (I)

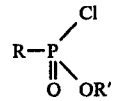

in which R stands for an alkyl group with 1 to 6 carbon atoms or an aryl group and R' stands for an alkyl group with 1 to 20 carbon atoms or an aryl group, which comprises: reacting a compound of general formula (I))

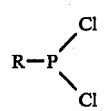

with a sulfuric acid monoester of general formula (III)

R'—O—SO$_3$H    (III)

the substituents R and R' in formulae (II) and (III) respectively, having the meanings given above, the reactants being used in about equimolar proportions and the reaction being effected at a temperature of from −20° C. to 50° C. if desired in the presence of an inert solvent; terminating the reaction and separating the phosphonic acid ester chloride from the reaction mixture by subjecting this latter to distillation under vacuum.

In general formula (II) the substituent R preferably stands for a methyl, ethyl or phenyl group and substituent R' in formula (III) preferably stands for a methyl, ethyl, isobutyl, hexadecyl or phenyl group.

The reactants of formulae (II) and (III) should preferably be used in a ratio of 1–1.2:1. In the event of the reaction being carried out in the presence of a diluent or solvent for the reactants, it is good practice to use diethylether or dichloroethane. Since the reaction takes an exothermal course, it may be preferable for the reaction mixture to be cooled and for the reaction temperature to be maintained within the range 0° to 10° C.

In carrying out the process of this invention, reactant (II) should preferably be added dropwise to a solution of reactant (III) in the inert solvent, or inversely. Reactant (III) is obtainable by known processes, e.g. by that described in Houben-Weyl, Methoden der organischen Chemie, volume 12/1 (1963). A further feature of the present process provides for reactant (III) to be prepared in the presence of the inert solvent e.g. by reacting chlorosulfonic acid with the alcohol corresponding to substituent R', and for reactant (II) to be dropped into the reaction mixture. It is possible for the chlorosulfonic acid to be replaced by a SO$_3$/dioxane addition product.

In clear contrast with prior art methods the present process basically is a one-step process, during which the phosphorus in reactant (II) is oxidized from oxidation stage 3 to oxidation stage 5 and a halogen atom is simultaneously replaced by an ester group, in just one reaction step. A further beneficial effect resides in that the exothermal reaction takes place under mild conditions yielding desirable final product together with gaseous materials only which are easy to separate therefrom.

The phosphonic acid ester chlorides obtained by the process of this invention are valuable intermediates which are used in the production of plant protecting agents, flame-retardant agents and plastics addends.

The following Examples illustrate the invention.

EXAMPLE 1

118 g (1.01 mol) chlorosulfonic acid (within 45 minutes), 75.1 g (1.01 mol) isobutanol (within 1 hour) and 121.7 g (1.04 mol) dichloromethylphosphane (within 2 hours) were successively introduced dropwise under nitrogen into 150 cm$^3$ diethylether placed in a 1-liter multi-necked flask which was provided with a stirrer, inside thermometer, reflux condenser and dropping funnel. By cooling with ice water, the temperature was maintained between 0° and 5° C. during the entire reaction. Hydrogen chloride and sulfur dioxide which were formed during the reaction were removed from the inert gas stream by scrubbing it with water or sodium hydroxide solution in a scrubbing zone downstream of the flask. Next, diethylether, dissolved hydrogen chloride and sulfur dioxide were separated under vacuum from the reaction mixture at room temperature. 169 g crude product was obtained. $^{31}$P-NMR-spectroscopy indicated 80% of the phosphorus used had undergone conversion to methanephosphonic acid isobutylester chloride, 7% to methanephosphonic acid dichloride and 8% to methanephosphonic acid diisobutylester.

The crude product was distillatively purified with partial decomposition by dropping it into a Vigreux column heated to 70° C. At a boiling temperature of 46°-50° C. under a pressure of 0.5 to 0.4 mm of mercury, it distilled over into the receiver in the form of a colorless liquid.

112 g distillate was obtained. 94% was methanephosphonic acid isobutylester chloride and 6% was methanephosphonic acid dichloride.

The yield after distillation was 106.9 g (0.63 mol) methanephosphonic acid isobutylester chloride, corresponding to 60.3% of the theoretical.

EXAMPLE 2

As in Example 1, 139.4 g (1.2 mols) chlorosulfonic acid (within 45 minutes), 89.0 g (1.2 mols) isobutanol (within 40 minutes) and 158 g (1.206 mols) dichloroethylphosphane (within 4 hours) were added to 150 cm$^3$ diethylether. Diethylether, hydrogen chloride and sulfur dioxide were separated and 225 g crude product was obtained. 82% of the phosphorus used was in the crude product in the form of ethanephosphonic acid isobutylester chloride which was distilled in a heated Vigreux column. The boiling point of the ester chlorides was 56° to 58° C. under 0.1 mm mercury. 146.3 distillate of which 93% was ethanephosphonic acid isobutylester chloride and 7% was ethanephosphonic acid dichloride was obtained.

The yield after distillation was 138 g (0.75 mol) ethanephosphonic acid isobutylester chloride, corresponding to 62% of the theoretical.

EXAMPLE 3

As in Example 1, 123.6 g (1.06 mols) chlorosulfonic acid, 99.8 g (1.06 mols) phenol and 128.7 g (1.1 mols) dichloromethylphosphane were reacted in the presence of 150 cm$^3$ diethylether while cooling with ice water. The solvent, hydrogen chloride and sulfur dioxide were separated and 217 g crude product was obtained. 44% of the phosphorus used was methanephosphonic acid phenylester chloride, 14.3% was methanephosphonic acid diphenylester and 3.6% was methanephosphonic acid dichloride. The crude product was distilled and 71.5 g distillate was obtained. It had a boiling point of 94° C. under 0.02 mm mercury. $^{31}$P-NMR-spectroscopy indicated that 89% was methanephosphonic acid phenylester chloride, 1.7% was methanephosphonic acid diphenylester and 2% was methanephosphonic acid dichloride.

The yield after distillation was 68.7 g (0.36 mol) methanephosphonic acid phenylester chloride, corresponding to 32.8% of the theoretical.

EXAMPLE 4

As in Example 1, 24 g (0.21 mol) chlorosulfonic acid was dropped within 45 minutes into 200 cm$^3$ diethylether while cooling with ice water. By means of a dosing feeder with worm conveyor 49.8 g (0.21 mol) 1-hexadecanol ($C_{16}H_{33}OH$) was introduced within 45 minutes and 25.9 g (0.22 mol) dichloromethylphosphane was successively introduced within 30 minutes into the clear colorless solution. The reaction product was white solid material which was obtained in a yield of 69 g, after removal of liquid and dissolved gaseous constituents. $^{31}$P-NMR-spectroscopy indicated that 83% of the phosphorus was in the form of methanephosphonic acid hexadecylester chloride and 15% was in the form of methanephosphonic acid dihexadecylester.

EXAMPLE 5

91.7 g (0.79 mol) chlorosulfonic acid was introduced into an apparatus as described in Example 1 and 36.4 g (0.79 mol) ethanol (within 75 minutes) and 106.6 g (0.81 mol) dichloroethylphosphane (within 2 hours) were separately added dropwise at 0° to 5° C. while cooling with ice. The reaction mixture was stripped for 1 h at room temperature under water jet vacuum so as to be freed from dissolved hydrogen chloride and sulfur dioxide. 122 g crude product was obtained, in which 34.2% of the phosphorus used was in the form of ethanephosphonic acid ethylester chloride. The product was distilled and a colorless liquid which had a boiling point of 30°-32° C. under 0.05 to 0.07 mm mercury was obtained. 63.3% of the phosphorus was in the form of ethanephosphonic acid ethylester chloride and 23.2% was in the form of ethanephosphonic acid dichloride; further constituents were not identified.

EXAMPLE 6

609 g sulfur trioxide-dioxane addition product, which contained 143.9 g (1.8 mols) sulfur trioxide and was dissolved in 400 g dichloroethane, was reacted with 137.1 g (1.85 mols) isobutanol, and a solution of sulfuric acid monoisobutylester in dichloroethane was obtained. 66 g of this solution, which contained 49 g (0.32 mol) sulfuric acid monoisobutylester, was added dropwise within 1 hour to 59.5 g (0.33 mol) dichlorophenylphosphane. The whole was initially heated for a short while to 30° C. and then cooled with water to maintain the reaction temperature at 20° C. Next, the reaction mixture was stirred for 4 hours at room temperature, stripped under a vacuum of 1 mm mercury and at a temperature of up to 30° C. 79 g of a brown, medium-viscous crude product was obtained. $^{31}$P-NMR-spectroscopy indicated that 41% of the phosphorus used was present in the crude product in the form of benzenephosphonic acid isobutylester chloride.

EXAMPLE 7

As described in Example 6, 59.6 g (0.33 mol) dichlorophenylphosphane was reacted within 85 minutes with 36 g (0.32 mol) sulfuric acid monomethylester, the ester being added to the phosphane. The reaction mixture was stripped at temperatures of up to 30° C. under a vacuum of up to 1 mm mercury, and a brown, medium-viscous liquid which contained 29% of the phosphorus in the form of benzenephosphonic acid monomethylester chloride was obtained.

We claim:

1. A process for making phosphonic acid ester chlorides of the general formula (I)

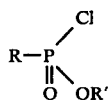
(I)

in which R stands for an alkyl group with 1 to 6 carbon atoms or an aryl group and R' stands for an alkyl group with 1 to 20 carbon atoms or an aryl group, which comprises: reacting a compound of general formula (II)

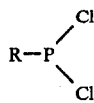
(II)

with a sulfuric acid monoester of general formula (III)

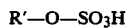
(III)

R and R' in formulae (II) and (III) respectively, having the meanings given above, the reactants being used in about equimolar proportions and the reaction being effected at a temperature of from $-20°$ C. to 50° C.; terminating the reaction and separating the phosphonic acid ester chloride from the reaction mixture by subjecting this latter to distillation under vacuum.

2. The process as claimed in claim 1, wherein R stands for a methyl, ethyl or phenyl group and R' stands for a methyl, ethyl, isobutyl, hexadecyl or phenyl group.

3. The process as claimed in claim 1, wherein reactant (II) and reactant (III) are used in a molar ratio of 1-1.2:1.

4. The process as claimed in claim 1, wherein the reaction temperature is 0° to 10° C.

5. The process as claimed in claim 1, wherein the reaction is effected in the presence of an inert solvent.

6. The process as claimed in claim 5, wherein the inert solvent is selected from diethylether or dichlorethane.

7. The process as claimed in claim 1, wherein reactant (II) is added dropwise while cooling, if desired, to a solution of reactant (III) in the inert solvent.

* * * * *